(12) United States Patent  
Morita

(10) Patent No.: US 8,724,230 B2
(45) Date of Patent: May 13, 2014

(54) ENDOSCOPE OBJECTIVE OPTICAL SYSTEM

(71) Applicant: Olympus Medical Systems Corp., Tokyo (JP)

(72) Inventor: Kazuo Morita, Tokyo (JP)

(73) Assignee: Olympus Medical Systems Corp., Tokyo (JP)

(*) Notice: Subject to any disclaimer, the term of this patent is extended or adjusted under 35 U.S.C. 154(b) by 0 days.

(21) Appl. No.: 13/734,141

(22) Filed: Jan. 4, 2013

(65) Prior Publication Data

US 2013/0163092 A1 Jun. 27, 2013

Related U.S. Application Data

(63) Continuation of application No. PCT/JP2012/065028, filed on Jun. 12, 2012.

(30) Foreign Application Priority Data

Jun. 29, 2011 (JP) ................................. 2011-144338

(51) Int. Cl.
*G02B 15/02* (2006.01)

(52) U.S. Cl.
USPC .......................................... 359/674; 359/672

(58) Field of Classification Search
USPC ................... 359/656–661, 672–675
See application file for complete search history.

(56) References Cited

U.S. PATENT DOCUMENTS

| 4,596,447 A * | 6/1986 | Yamada et al. ............... 359/674 |
| 4,741,605 A * | 5/1988 | Alfredsson et al. ........... 359/675 |
| 5,547,457 A | 8/1996 | Tsuyuki et al. |
| 2009/0051764 A1 | 2/2009 | Ishii et al. |

FOREIGN PATENT DOCUMENTS

| EP | 2 011 431 | 1/2009 |
| JP | 47-023224 | 6/1972 |
| JP | 04-208915 | 7/1992 |
| JP | 06-222263 | 8/1994 |
| JP | 11-249014 | 9/1999 |
| JP | 2001-221958 | 8/2001 |
| JP | 2007-289278 | 11/2007 |

OTHER PUBLICATIONS

International Search Report, dated Jul. 31, 2012, issued in corresponding International Application No. PCT/JP2012/065028.

* cited by examiner

*Primary Examiner* — Scott J Sugarman
(74) *Attorney, Agent, or Firm* — Kenyon & Kenyon LLP

(57) ABSTRACT

Provided is an endoscope objective optical system that allows close-up observation while ensuring sufficient image brightness. Provided is an endoscope objective optical system consisting of a front group, an aperture stop, and a back group disposed in order from an object side; and a meniscus lens that can be inserted in and removed from an optical path between the aperture stop and the front group or the back group, with a convex surface thereof facing the aperture stop side.

10 Claims, 14 Drawing Sheets

ENDOSCOPE OBJECTIVE OPTICAL SYSTEM

CROSS-REFERENCE TO RELATED APPLICATIONS

This is a continuation of International Application PCT/JP2012/065028, with an international filing date of Jun. 12, 2012, which is hereby incorporated by reference herein in its entirety. This application claims the benefit of Japanese Patent Application No. 2011-144338, the content of which is incorporated herein by reference.

TECHNICAL FIELD

The present invention relates to an endoscope objective optical system.

BACKGROUND ART

A known optical system for endoscopes in the related art allows close-up observation by varying the aperture diameter of an aperture stop and decreasing the aperture diameter to enlarge the depth of field (for example, see PTL 1).

CITATION LIST

Patent Literature

{PTL 1} Japanese Unexamined Patent Application, Publication No. 2007-289278

SUMMARY OF INVENTION

Technical Problem

The depth of field obtained by narrowing the aperture stop and the amount of light are in a mutually opposing relationship. Specifically, in the case of the optical system disclosed in PTL 1, a sufficient amount of light cannot be ensured during close-up observation, forming a dark image.

Solution to Problem

The present invention provides an endoscope objective optical system consisting of a front group, an aperture stop, and a back group disposed in order from an object side; and a meniscus lens that can be inserted in and removed from an optical path between the aperture stop and the front group or the back group, with a convex surface thereof facing the aperture stop side.

DESCRIPTION OF EMBODIMENT

An endoscope objective optical system 1 according to an embodiment of the present invention will be described hereinbelow with reference to FIGS. 1 to 3.

Figure 1:
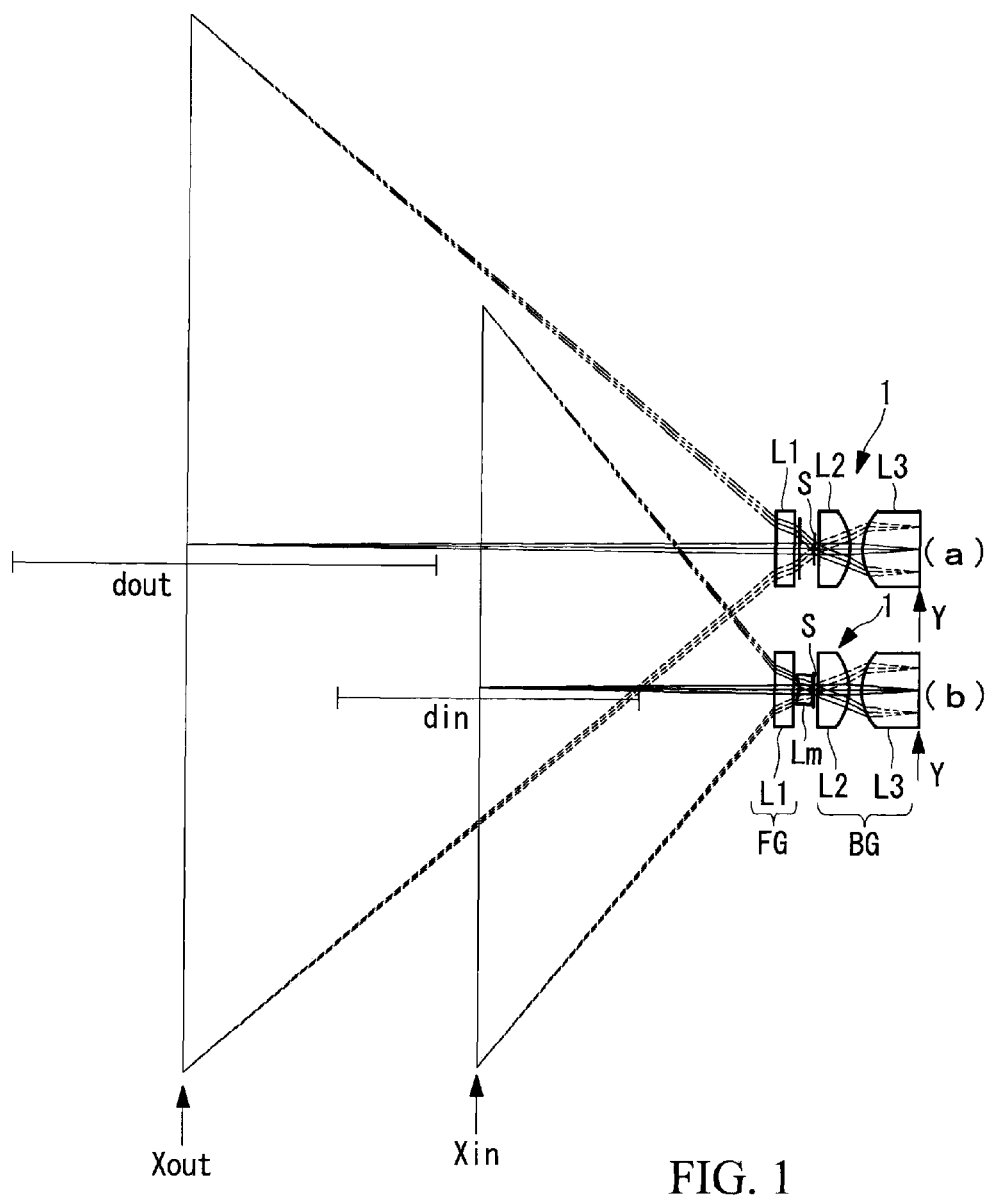
FIG. 1 is a diagram showing the overall configuration of an endoscope objective optical system according to an embodiment of the present invention.

As shown in FIG. 1, the endoscope objective optical system 1 according to this embodiment is equipped with a front group FG, an aperture stop S, and a back group BG, which are disposed in this order from the object side, and a meniscus lens Lm which is removably provided in an optical path between the front group FG and the aperture stop S.

The front group FG includes a parallel flat plate L1.

The back group BG includes, in order from the object side, a plano-convex lens L2 whose convex surface faces the image side and a plano-convex lens L3 whose convex surface faces the object side.

The meniscus lens Lm, whose convex surface faces the aperture stop S side, is movably provided between an inserted position where it is inserted in an optical path in the vicinity of the aperture stop S and a retracted position where it is removed from the optical path. In FIG. 1, (a) shows an ordinary observation state in which the meniscus lens Lm is disposed at the retracted position, and (b) shows a close-up observation state in which the meniscus lens Lm is disposed at the inserted position. In the drawing, arrows Xout and Xin indicate object planes in the ordinary observation state or the close-up observation state, respectively, arrows Y indicate imaging planes, and dout and din indicate the depths of field in the ordinary observation state or the close-up observation state, respectively.

Thus, this embodiment allows close-up observation by moving the focal position toward a near point merely by inserting the meniscus lens Lm in the optical path. At that time, there is no need to narrow the beam with the aperture stop S, which allows close-up observation to be performed while ensuring a sufficient amount of light, thus allowing a bright close-up image to be captured.

According to this embodiment, the lens diameter of the meniscus lens can be made small by inserting the meniscus lens in the vicinity of the aperture stop S, where the beam diameter is small. Thus, a space ensured for retracting the meniscus lens can be made small, which can reduce the diameter of the entire system.

Figure 2:
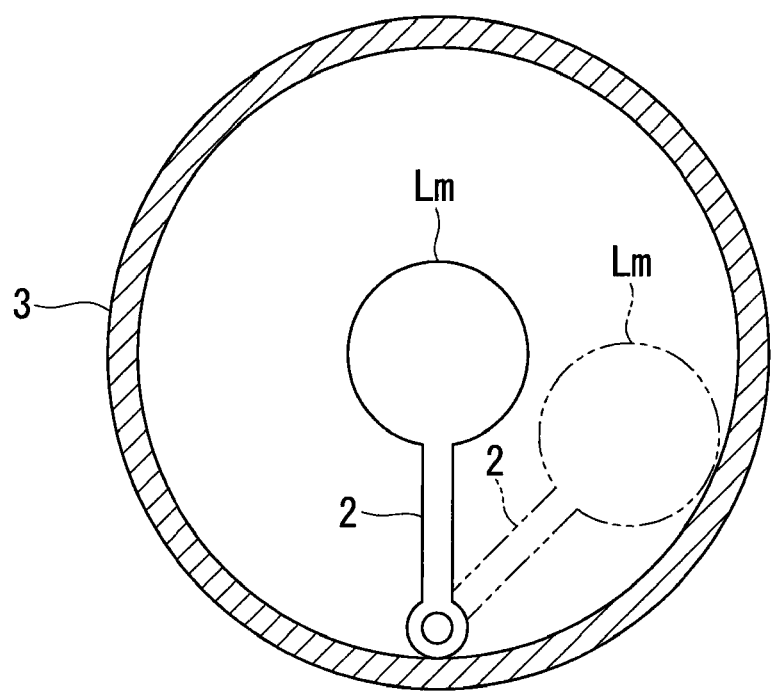
FIG. 2 is a diagram showing an example of a driving mechanism equipped with an arm member integrally formed with a meniscus lens.

FIG. 2 shows an example of a driving mechanism that moves the meniscus lens Lm between the inserted position indicated by a solid line and the retracted position indicated by a broken line. The driving mechanism is equipped with an arm member 2 that holds the meniscus lens Lm at one end and a motor (not shown) that pivots the meniscus lens Lm by rotating the other end of the arm member 2. Reference sign 3 denotes a lens barrel that accommodates the endoscope objective optical system 1. The arm member 2 is formed integrally with the meniscus lens Lm. This eliminates the need for a frame member for holding the meniscus lens Lm around the outer circumference of the meniscus lens Lm, thus allowing the diameter to be made small. In addition, compared with the meniscus lens manufactured by grinding, the meniscus lens Lm can be manufactured easily and cheaply by using a molded lens as a meniscus lens Lm.

This embodiment is configured such that the meniscus lens Lm is inserted in and removed from the vicinity of the object side of the aperture stop S; instead, the meniscus lens Lm may be inserted in and removed from the vicinity of the image side of the aperture stop S. Also in this case, the meniscus lens Lm is inserted in the optical path, with the convex surface thereof facing the aperture stop S. This also allows close-up observation by moving the focal position toward the near point merely by inserting the meniscus lens Lm in the optical path, thus allowing a bright close-up image to be captured.

Figure 3:
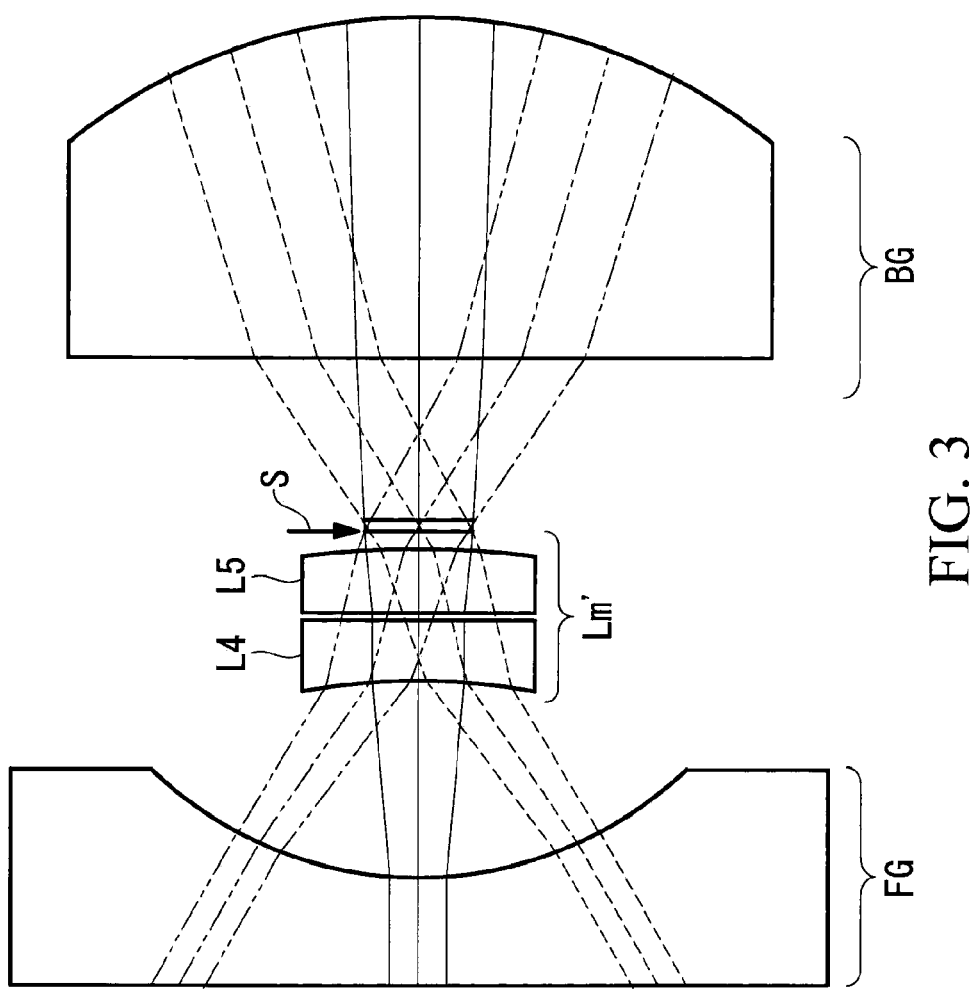
FIG. 3 is a diagram showing a modification of a meniscus lens constituted of a plurality of lenses.

As shown in FIG. 3, this embodiment may use a meniscus lens Lm' composed of a plurality of lenses instead of the single-element meniscus lens Lm. In the illustrated example, the meniscus lens Lm' is constituted of a plano-concave lens L4 and a plano-convex lens L5 which are mated with each other at the flat surfaces thereof.

This allows the meniscus lens Lm' having the same optical action as that of the single-element meniscus lens Lm to be manufactured at low cost.

In this embodiment described above, the front group FG may be a diverging lens system, the back group BG may be a converging lens system, the meniscus lens Lm can be inserted in and removed from the optical path between the aperture stop S and the front group FG, and the following Conditional Expression (1) may be satisfied.

$$0.9 \leq Fin/Fout \leq 1.1 \quad (1)$$

where Fin is the focal length of the entire system when the meniscus lens Lm is inserted in the optical path, and Fout is the focal length of the entire system when the meniscus lens Lm is retracted from the optical path.

Conditional Expression (1) defines a change in focal length when the meniscus lens Lm is inserted in and removed from the optical path. In other words, since a change in the field of view of an image displayed on a monitor when switching between the ordinary observation and the close-up observation can be suppressed by satisfying Conditional Expression (1), the focal position can be changed without causing the observer to feel a noticeable difference.

In this embodiment described above, the back group BG may be a converging lens system, the meniscus lens Lm can be inserted in and removed from between the aperture stop S and the back group BG, and the following Conditional Expression (2) may be satisfied.

$$1.1 < FOVout/FOVin < 1.5 \quad (2)$$

where, FOVout is a full angle of view when the meniscus lens Lm is retracted from the optical path, and FOVin is a full angle of view when the meniscus lens Lm is inserted in the optical path.

Conditional Expression (2) defines a change in the full angle of view when the meniscus lens Lm is inserted in and removed from the optical path. In other words, by satisfying Conditional Expression (2), the full angle of view is decreased when the meniscus lens Lm is inserted in the optical path, so that the field of view displayed on the monitor is decreased. That is, an image of the near point side can be displayed in an enlarged scale. This allows the area on the near point side to be observed in more detail.

In this embodiment described above, the following Conditional Expression (3) may be satisfied.

$$1.5 \leq D/A \leq 3 \quad (3)$$

where A is the inside diameter of the aperture stop S, and D is the outside diameter of the meniscus lens Lm.

Conditional Expression (3) defines the outside diameter of the meniscus lens Lm relative to the inside diameter of the aperture stop S. In other words, by satisfying Conditional Expression (3), the lens diameter of the meniscus lens Lm can be suppressed while allowing the whole beam that has passed through the aperture stop S to pass through the meniscus lens Lm.

In this embodiment described above, the meniscus lens Lm may satisfy the following Conditional Expression (4).

$$-0.1 \leq P \leq 0.1 \quad (4)$$

where P is the power of the meniscus lens.

By satisfying Conditional Expression (4), displacement of the center of the field of view and the occurrence of aberrations can be suppressed even if the center position of the meniscus lens Lm is shifted more or less from the optical axis when the meniscus lens Lm is inserted in the optical path. This can prevent the observer from being given a noticeable difference when the meniscus lens Lm is inserted or removed. Furthermore, since fine positioning precision is not required for the driving mechanism that drives the meniscus lens Lm, the driving mechanism can be manufactured at low cost.

In this embodiment described above, the following Conditional Expression (5) may be satisfied.

$$0.7 \leq L/Fout \leq 1.4 \quad (5)$$

where L is the intersurface distance between front and back lenses that sandwich the aperture stop S, and Fout is the focal length of the entire system when the meniscus lens Lm is retracted from the optical path.

Conditional Expression (5) defines the size of the spaces in front of and behind the aperture stop S in which the meniscus lens Lm and the driving mechanism that drives the meniscus lens Lm are disposed. In other words, by satisfying Conditional Expression (5), a sufficient space for the meniscus lens Lm and the driving mechanism can be ensured while suppressing the overall size.

In this embodiment described above, the effective F-number when the meniscus lens Lm is retracted from the optical path may be greater than or equal to 5.

This can suppress the lens diameter of the meniscus lens Lm by suppressing the diameter of the beam passing through the aperture stop S while ensuring a sufficient amount of light.

EXAMPLES

Next, Examples 1 to 6 of the foregoing embodiment will be described hereinbelow with reference to FIGS. 4 to 14.

In the lens data shown in the examples, r denotes the radius of curvature (mm), d is the intersurface distance (mm), nd is the refractive index at the d-line, vd is the Abbe number at the d-line, and φ denotes the lens radius. For the aperture stop (S), an inside diameter (aperture diameter) (mm) is shown instead of the lens radius (mm). Furthermore, OBJ appearing under surface number denotes an object plane, and IMG denotes an image plane. The lens data and the attached lens cross-sectional views include a meniscus lens inserted in the optical path.

Example 1

Figure 4:
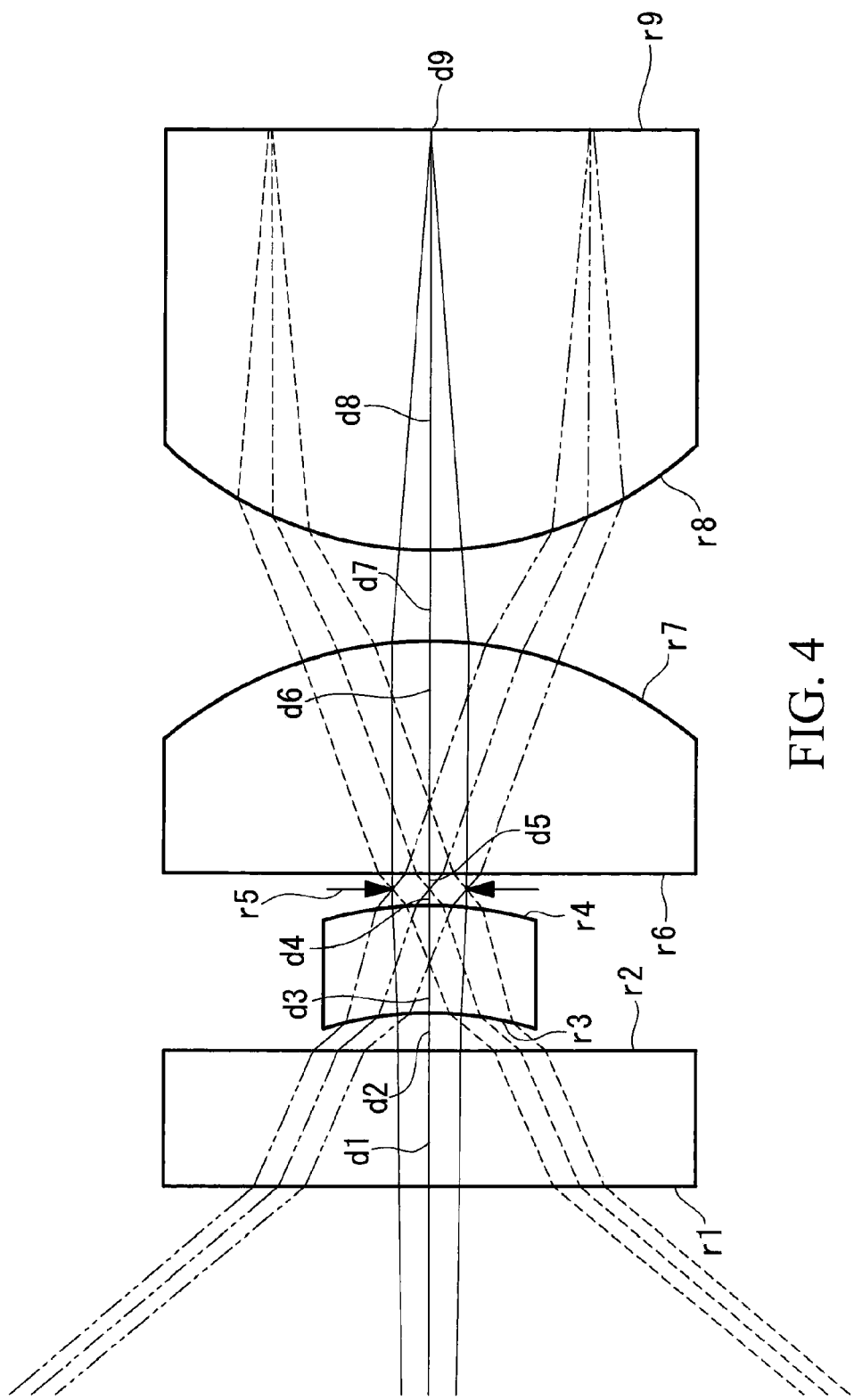
FIG. 4 is a lens cross-sectional view of an endoscope objective optical system according to Example 1 of the present invention.

As shown in FIG. 4, an endoscope objective optical system according to Example 1 of the present invention is configured such that the front group is constituted of a parallel flat plate, and the back group is constituted of, in order from the object side, a plano-convex lens whose convex surface faces the image side and a plano-convex lens whose convex surface faces the object side. A meniscus lens is removably provided between the front group and an aperture stop. The lens data and miscellaneous data of the thus-configured endoscope objective optical system according to Example 1 are as follows:

| Lens Data | | | | | |
|---|---|---|---|---|---|
| Surface number | r | d | nd | vd | φ |
| OBJ | ∞ | d0 (variable) | | | 10.727 |
| 1 | ∞ | 0.527 | 1.883 | 40.8 | 1.055 |
| 2 | ∞ | 0.148 | | | 1.055 |
| 3 | −1.455 | 0.422 | 1.883 | 40.8 | 0.422 |
| 4 | −1.569 | 0.063 | | | 0.422 |
| 5 (S) | ∞ | 0.063 | | | 0.148 |
| 6 | ∞ | 0.904 | 1.883 | 40.8 | 1.055 |
| 7 | −1.643 | 0.354 | | | 1.055 |
| 8 | 1.564 | 1.635 | 1.883 | 40.8 | 1.055 |
| 9 | ∞ | 0.000 | | | 1.055 |
| IMG | ∞ | 0.000 | | | 0.653 |

| Miscellaneous Data | | |
|---|---|---|
| | Ordinary observation | Close-up observation |
| d0 | 16.878 | 8.439 |

Example 2

Figure 5:
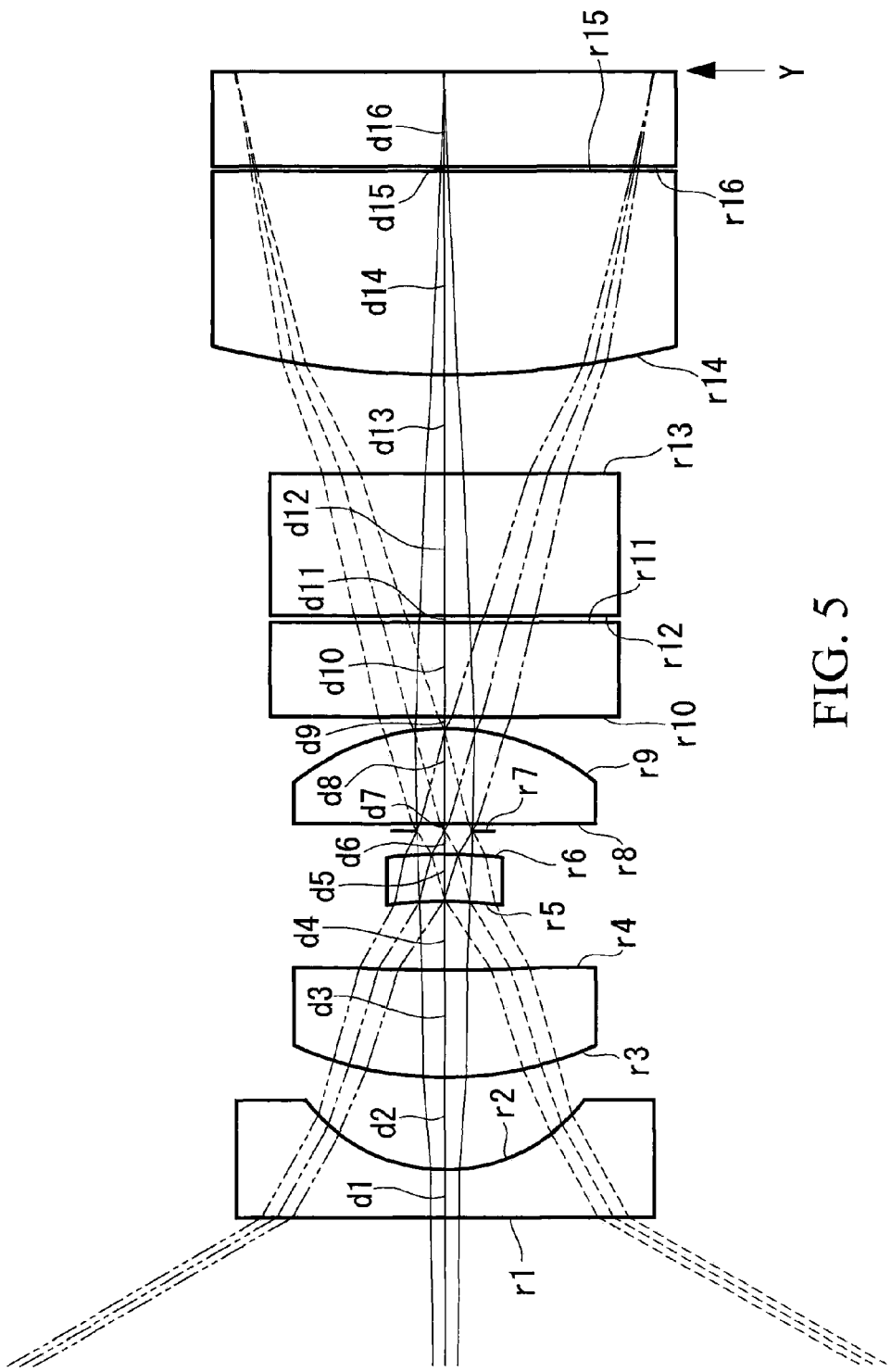
FIG. 5 is a lens cross-sectional view of an endoscope objective optical system according to Example 2 of the present invention.

As shown in FIG. 5, an endoscope objective optical system according to Example 2 of the present invention is configured such that the front group is a diverging lens system constituted of, in order from the object side, a plano-concave lens whose concave surface faces the image side and a meniscus lens whose convex surface faces the object side. The back group is a converging lens system constituted of, in order from the object side, a plano-convex lens whose convex surface faces the image side, two parallel flat plates, a plano-convex lens whose convex surface faces the object side, and a parallel flat plate. The meniscus lens is removably provided between the front group and an aperture stop. The lens data and miscellaneous data of the thus-configured endoscope objective optical system according to Example 2 are as follows:

| Lens Data | | | | | |
|---|---|---|---|---|---|
| Surface number | r | d | nd | vd | φ |
| OBJ | ∞ | d0 (variable) | | | 9.944 |
| 1 | ∞ | 0.204 | 1.768 | 72.2 | 0.917 |
| 2 | 0.771 | 0.400 | | | 0.612 |
| 3 | 1.658 | 0.468 | 1.923 | 18.9 | 0.663 |
| 4 | 6.385 | 0.297 | | | 0.376 |
| 5 | −2.144 | 0.204 | 1.883 | 40.8 | 0.255 |
| 6 | −2.181 | 0.099 | | | 0.255 |
| 7 (S) | ∞ | 0.031 | | | 0.122 |
| 8 | ∞ | 0.412 | 1.772 | 49.6 | 0.663 |
| 9 | −1.058 | 0.051 | | | 0.663 |
| 10 | ∞ | 0.408 | 1.523 | 58.5 | 0.765 |
| 11 | ∞ | 0.031 | | | 0.765 |
| 12 | ∞ | 0.612 | 1.523 | 75.0 | 0.765 |
| 13 | ∞ | 0.424 | | | 0.765 |
| 14 | 4.279 | 0.877 | 1.523 | 64.1 | 1.019 |
| 15 | ∞ | 0.020 | 1.51 | 63.8 | 1.019 |
| 16 | ∞ | 0.408 | 1.611 | 50.2 | 1.019 |
| IMG | ∞ | 0.000 | | | 0.930 |

| Miscellaneous Data | | |
|---|---|---|
| | Ordinary observation state | Close-up observation state |
| d0 | 10.149 | 5.207 |
| Focal length of the entire system | 1.000 | 0.959 |

Example 3

Figure 6:
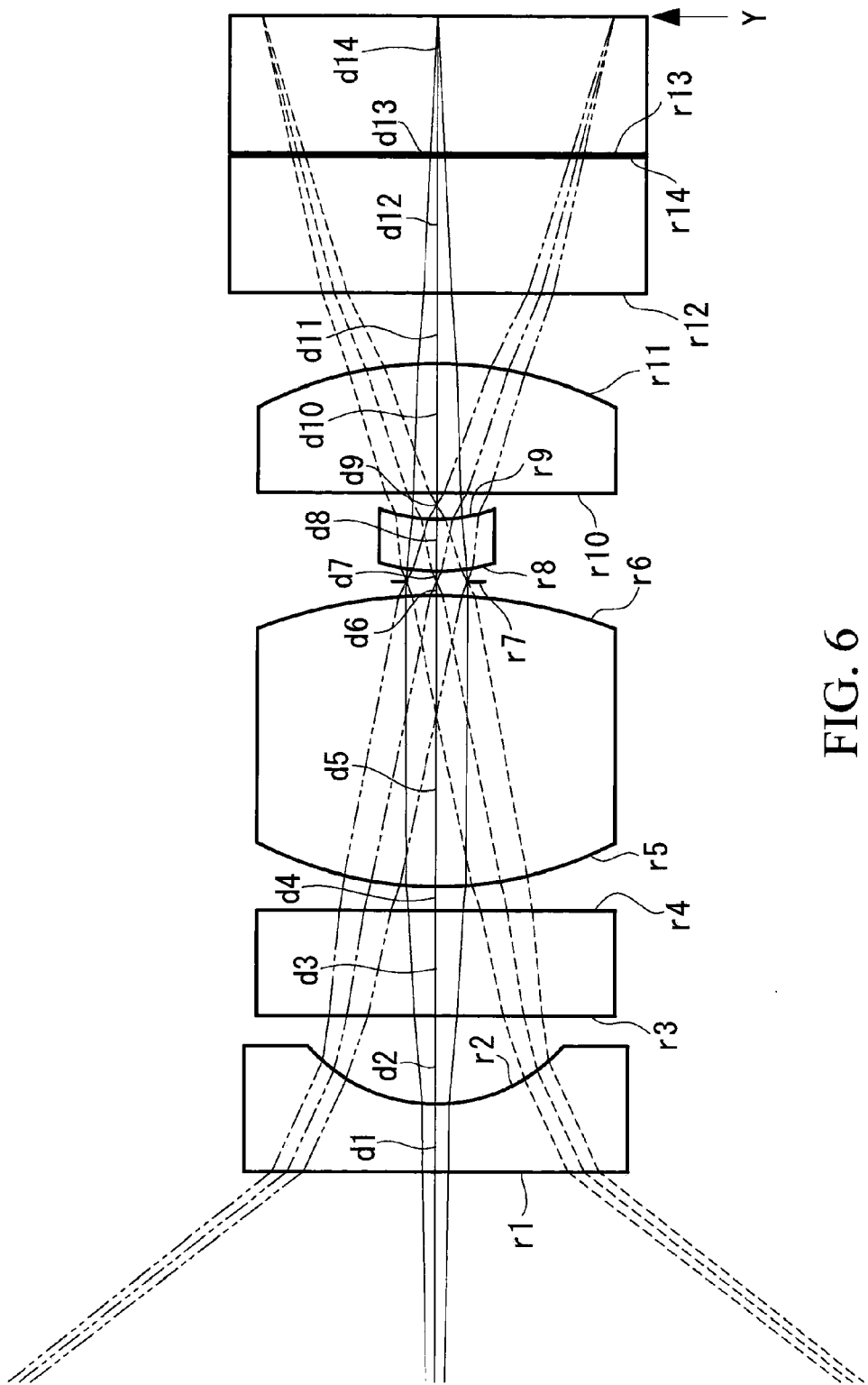
FIG. 6 is a lens cross-sectional view of an endoscope objective optical system according to Example 3 of the present invention.

As shown in FIG. 6, an endoscope objective optical system according to Example 3 of the present invention is configured such that the front group is constituted of, in order from the object side, a plano-concave lens whose concave surface faces the image side, a parallel flat plate, and a biconvex lens. The back group is a converging lens system constituted of, in order from the object side, a plano-convex lens whose convex surface faces the image side and two parallel flat plates. The meniscus lens is removably provided between an aperture stop and the back group. The lens data and miscellaneous data of the thus-configured endoscope objective optical system according to Example 3 are as follows. In the endoscope objective optical system of this example, FOVout/FOVin=1.14 holds, which satisfies Conditional Expression (2).

| Lens Data | | | | | |
|---|---|---|---|---|---|
| Surface number | r | d | nd | vd | φ |
| OBJ | ∞ | d0 (variable) | | | 6.170 |
| 1 | ∞ | 0.359 | 1.883 | 40.8 | 1.032 |
| 2 | 0.919 | 0.470 | | | 0.688 |
| 3 | ∞ | 0.557 | 1.516 | 75.0 | 0.963 |
| 4 | ∞ | 0.126 | | | 0.963 |
| 5 | 2.116 | 1.544 | 2.00 | 28.3 | 0.963 |
| 6 | −2.722 | 0.072 | | | 0.963 |
| 7 (S) | ∞ | 0.055 | | | 0.165 |
| 8 | 1.092 | 0.275 | 1.883 | 40.8 | 0.310 |
| 9 | 0.919 | 0.138 | | | 0.310 |
| 10 | ∞ | 0.682 | 1.516 | 64.1 | 0.963 |
| 11 | −2.124 | 0.373 | | | 0.963 |

-continued

| | | | | | |
|---|---|---|---|---|---|
| 12 | ∞ | 0.718 | 1.516 | 64.1 | 1.122 |
| 13 | ∞ | 0.018 | 1.51 | 64.1 | 1.122 |
| 14 | ∞ | 0.718 | 1.52 | 64.1 | 1.122 |
| IMG | ∞ | 0.000 | | | 1.122 |

| Miscellaneous Data | | |
|---|---|---|
| | Ordinary observation state | Close-up observation state |
| d0 | 11.011 | 4.129 |
| Full angle of view | 120° | 104.913° |

Example 4

Figure 7:
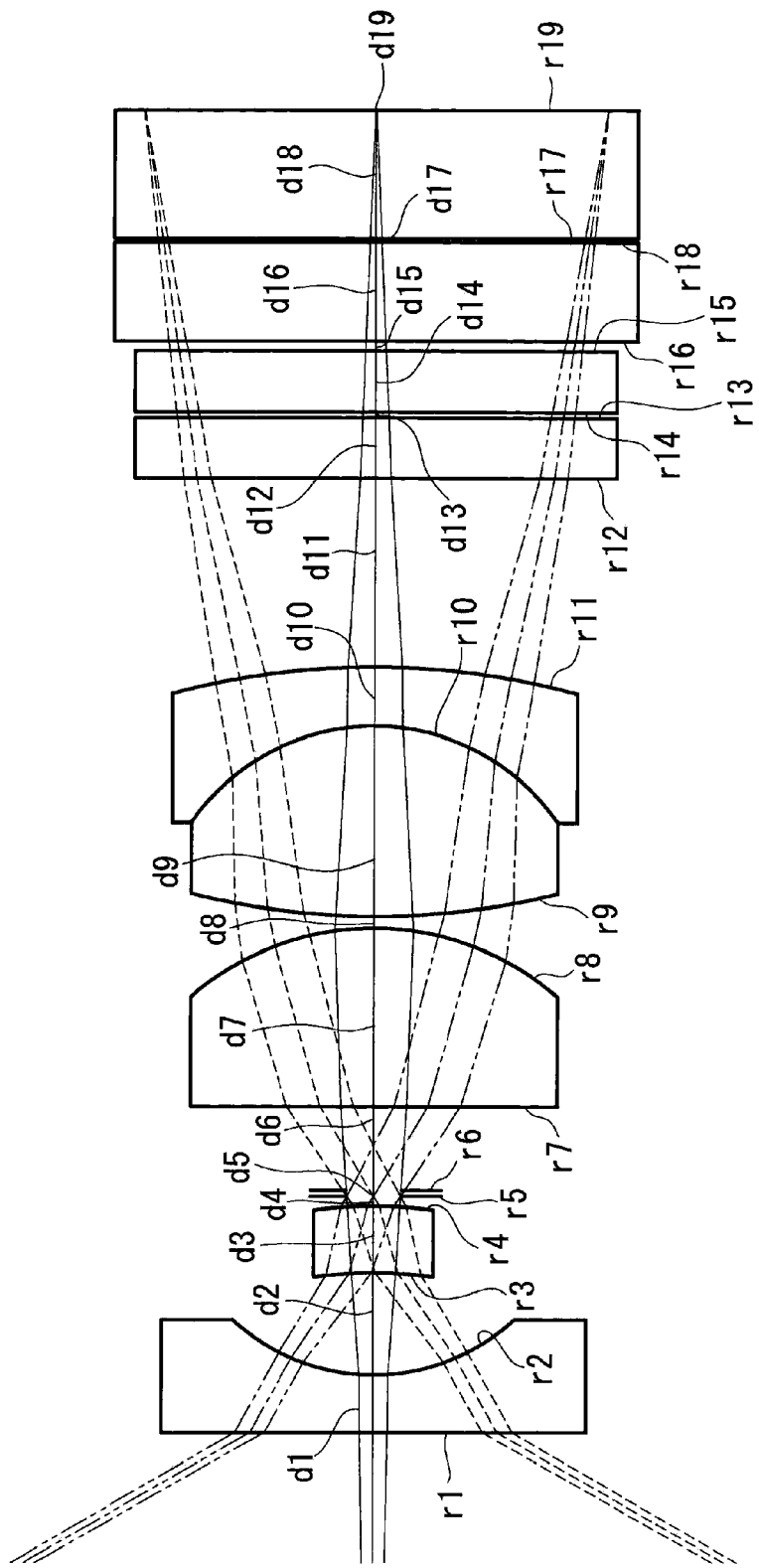
FIG. 7 is a lens cross-sectional view of an endoscope objective optical system according to Example 4 of the present invention.

As shown in FIG. 7, an endoscope objective optical system according to Example 4 of the present invention is configured such that the front group is a diverging lens system constituted of a plano-concave lens whose concave surface faces the image side. The back group is a converging lens system constituted of, in order from the object side, a plano-convex lens whose convex surface faces the image side, a combined lens composed of a biconvex lens and a meniscus lens, and four parallel flat plates. The meniscus lens is removably provided between the front group and an aperture stop. The lens data and miscellaneous data of the thus-configured endoscope objective optical system according to Example 4 are as follows.

Figure 8:
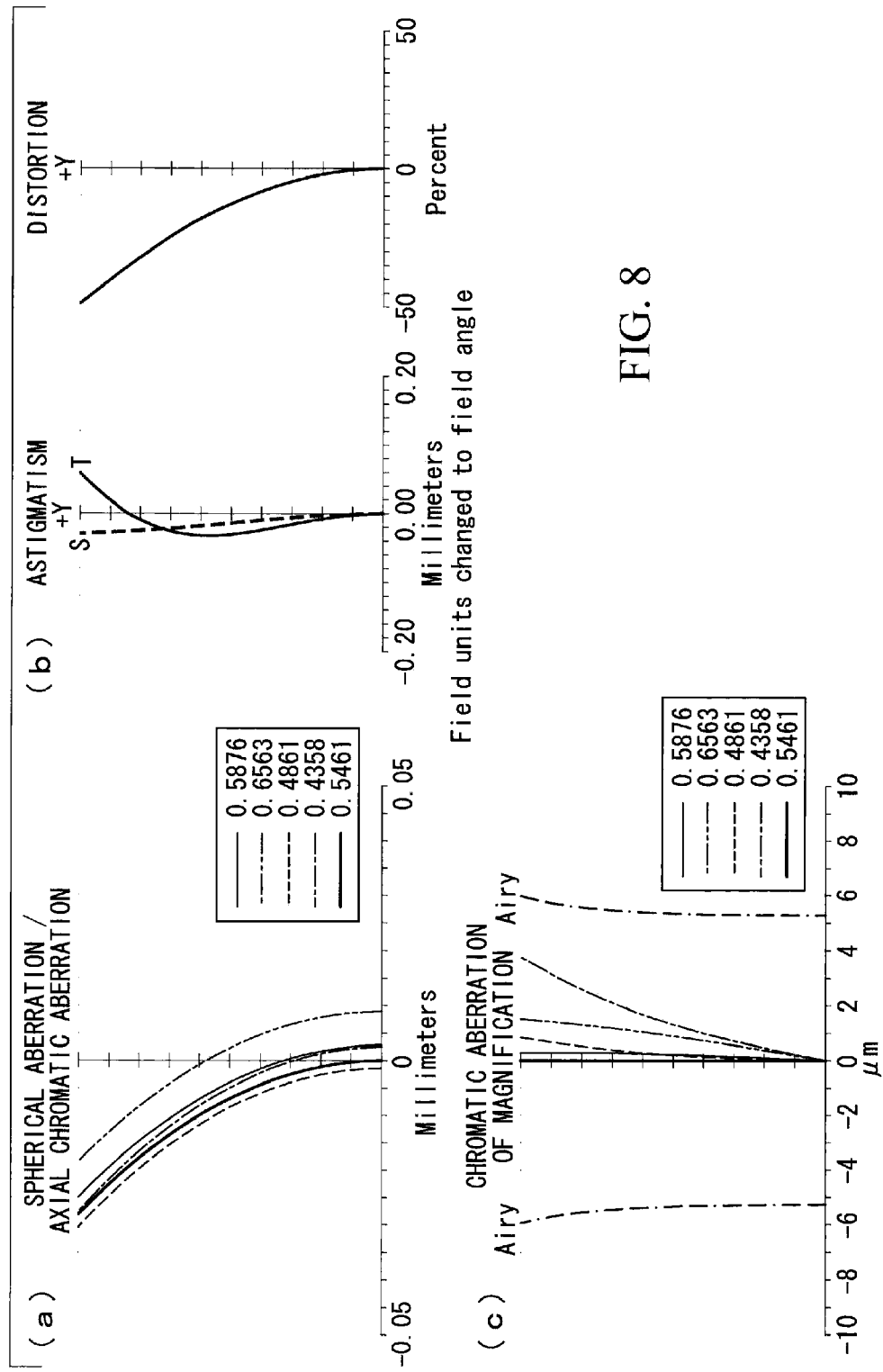
FIG. 8 is a diagram showing (a) spherical aberration/axial chromatic aberration, (b) astigmatism and distortion, and (c) magnification chromatic aberration of the endoscope objective optical system in FIG. 7 in an ordinary observation state.
Figure 9:
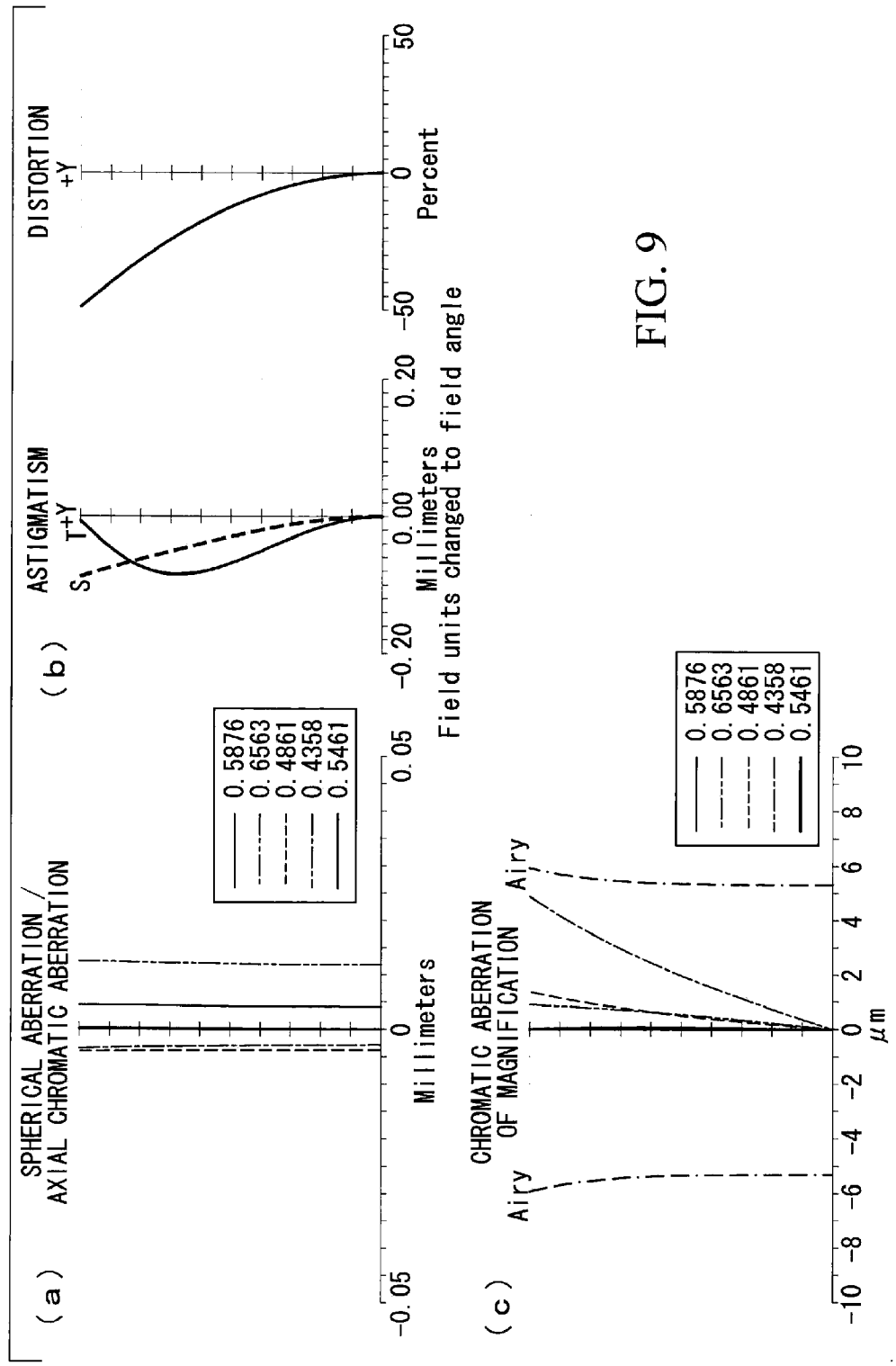
FIG. 9 is a diagram showing (a) spherical aberration/axial chromatic aberration, (b) astigmatism and distortion, and (c) magnification chromatic aberration of the endoscope objective optical system in FIG. 7 in a close-up observation state.
Figure 10:
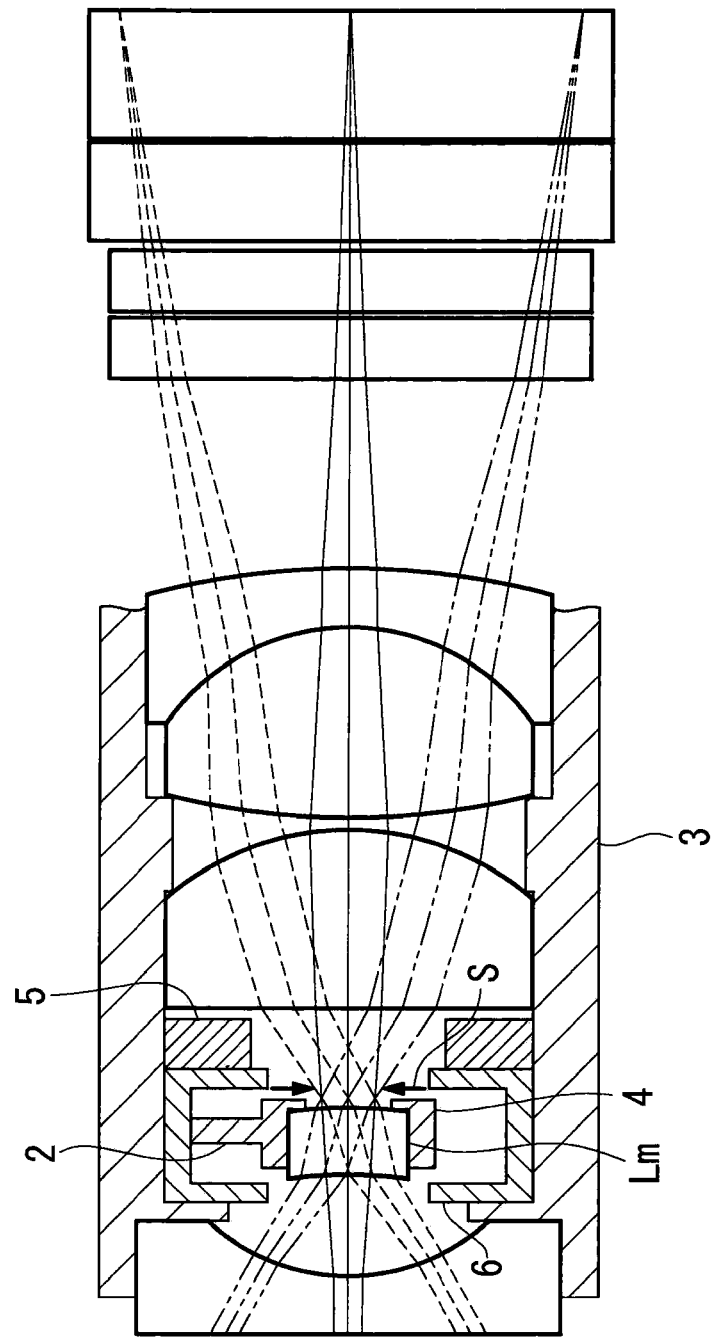
FIG. 10 is a diagram showing an example of a driving mechanism provided in the endoscope objective optical system in FIG. 7.

The endoscope objective optical system of this example satisfies Conditional Expression (1). Furthermore, the power P of the meniscus lens is 0.0387, which satisfies Conditional Expression (4). Furthermore, the intersurface distance L between the front and back surfaces that flank the aperture stop is 1.06, which satisfies Conditional Expression (5). Furthermore, the effective Fno. in the ordinary observation state is 7.9. Various aberration diagrams of the endoscope objective optical system according to this example in the ordinary observation state and the close-up observation state are shown in FIGS. 8 and 9, respectively. An example of a configuration in which the objective optical system according to this example is provided with a driving mechanism for driving the meniscus lens is shown in FIG. 10. Reference sign 4 denotes a frame member that holds the lens, reference sign 5 denotes a motor that drives the arm member 2, and reference sign 6 denotes a holding member that supports the arm member 2 and is fixed to the lens barrel 2.

| Lens Data | | | | | |
|---|---|---|---|---|---|
| Surface number | r | d | nd | vd | φ |
| OBJ | ∞ | d0 (variable) | | | 5.646 |
| 1 | ∞ | 0.223 | 1.768 | 71.7 | 0.847 |
| 2 | 0.831 | 0.404 | | | 0.562 |
| 3 | 1.873 | 0.264 | 1.883 | 40.8 | 0.239 |
| 4 | 1.845 | 0.039 | | | 0.239 |
| 5 (S) | ∞ | 0.023 | | | 0.108 |
| 6 | ∞ | 0.330 | | | 0.108 |
| 7 | ∞ | 0.701 | 1.883 | 40.8 | 0.732 |
| 8 | 1.125 | 0.046 | | | 0.732 |
| 9 | 3.066 | 0.752 | 1.518 | 58.9 | 0.732 |
| 10 | 0.894 | 0.231 | 1.923 | 18.9 | 0.732 |
| 11 | 3.185 | 0.739 | | | 0.809 |
| 12 | ∞ | 0.239 | 1.523 | 58.6 | 0.963 |
| 13 | ∞ | 0.023 | | | 0.963 |
| 14 | ∞ | 0.239 | 1.51 | 75.0 | 0.963 |
| 15 | ∞ | 0.039 | | | 0.963 |

-continued

| | | | | | |
|---|---|---|---|---|---|
| 16 | ∞ | 0.385 | 1.516 | 64.1 | 1.046 |
| 17 | ∞ | 0.015 | 1.51 | 64.1 | 1.046 |
| 18 | ∞ | 0.501 | 1.506 | 50.2 | 1.046 |
| 19 | ∞ | 0.000 | | | 1.046 |
| IMG | ∞ | 0.000 | | | 0.930 |

| Miscellaneous Data | | |
|---|---|---|
| | Ordinary observation state | Close-up observation state |
| d0 | 6.933 | 2.927 |
| Focal length of the entire system | 1.000 | 0.975 |

Example 5

Figure 11:
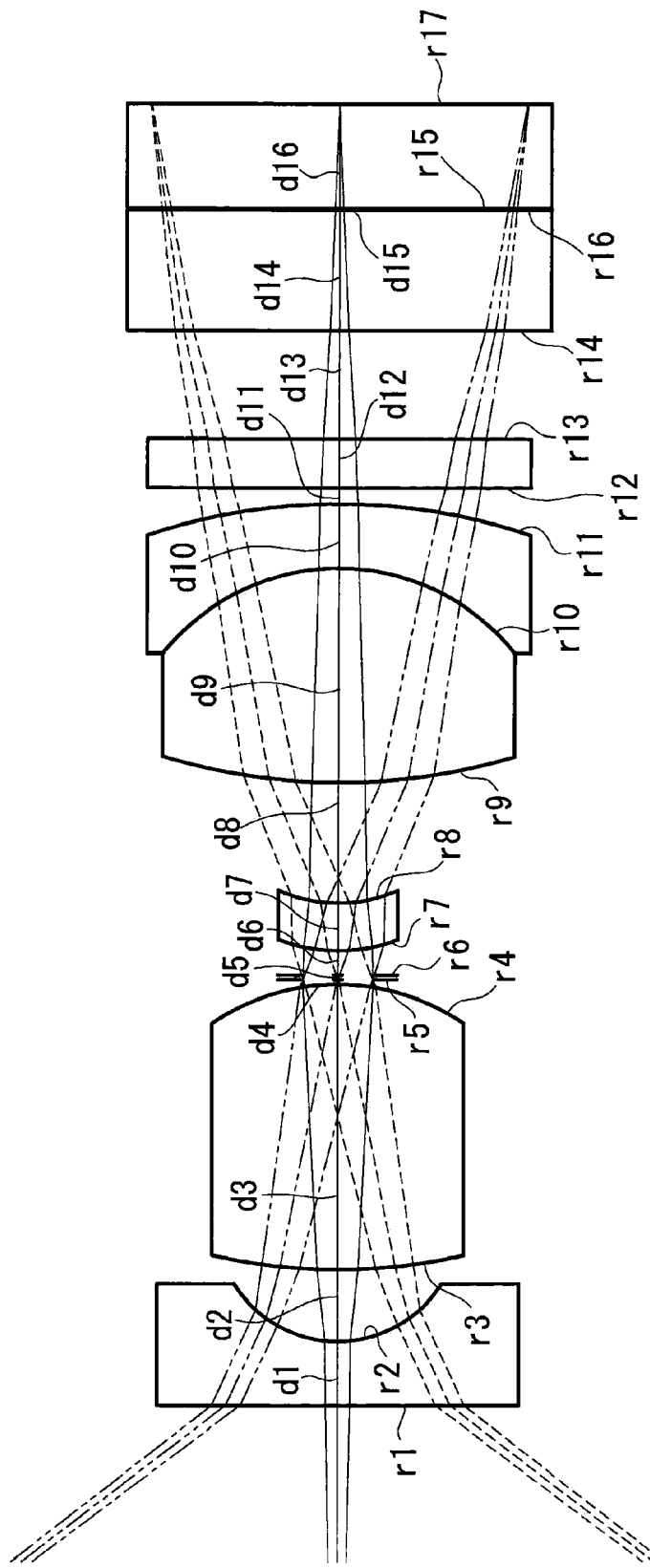
FIG. 11 is a lens cross-sectional view of an endoscope objective optical system according to Example 5 of the present invention.

As shown in FIG. 11, an endoscope objective optical system according to Example 5 of the present invention is configured such that the front group is constituted of, in order from the object side, a plano-concave lens whose concave surface faces the image side and a biconvex lens. The back group is a converging lens system constituted of, in order from the object side, a combined lens composed of a biconvex lens and a meniscus lens and three parallel flat plates. The meniscus lens is removably provided between an aperture stop and the back group. The lens data and miscellaneous data of the thus-configured endoscope objective optical system according to Example 5 are as follows.

Figure 12:
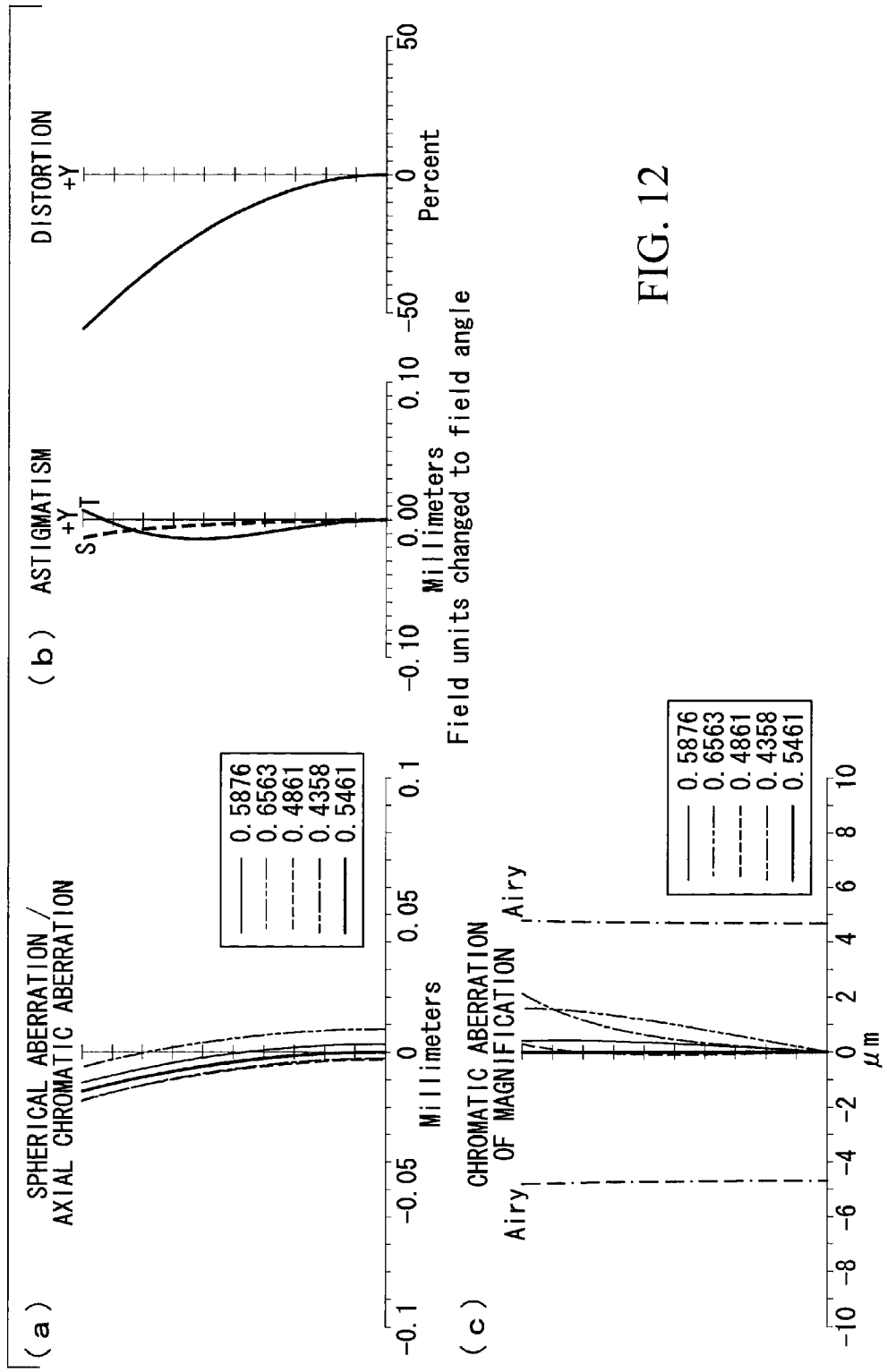
FIG. 12 is a diagram showing (a) spherical aberration/axial chromatic aberration, (b) astigmatism and distortion, and (c) magnification chromatic aberration of the endoscope objective optical system in FIG. 11 in an ordinary observation state.
Figure 13:
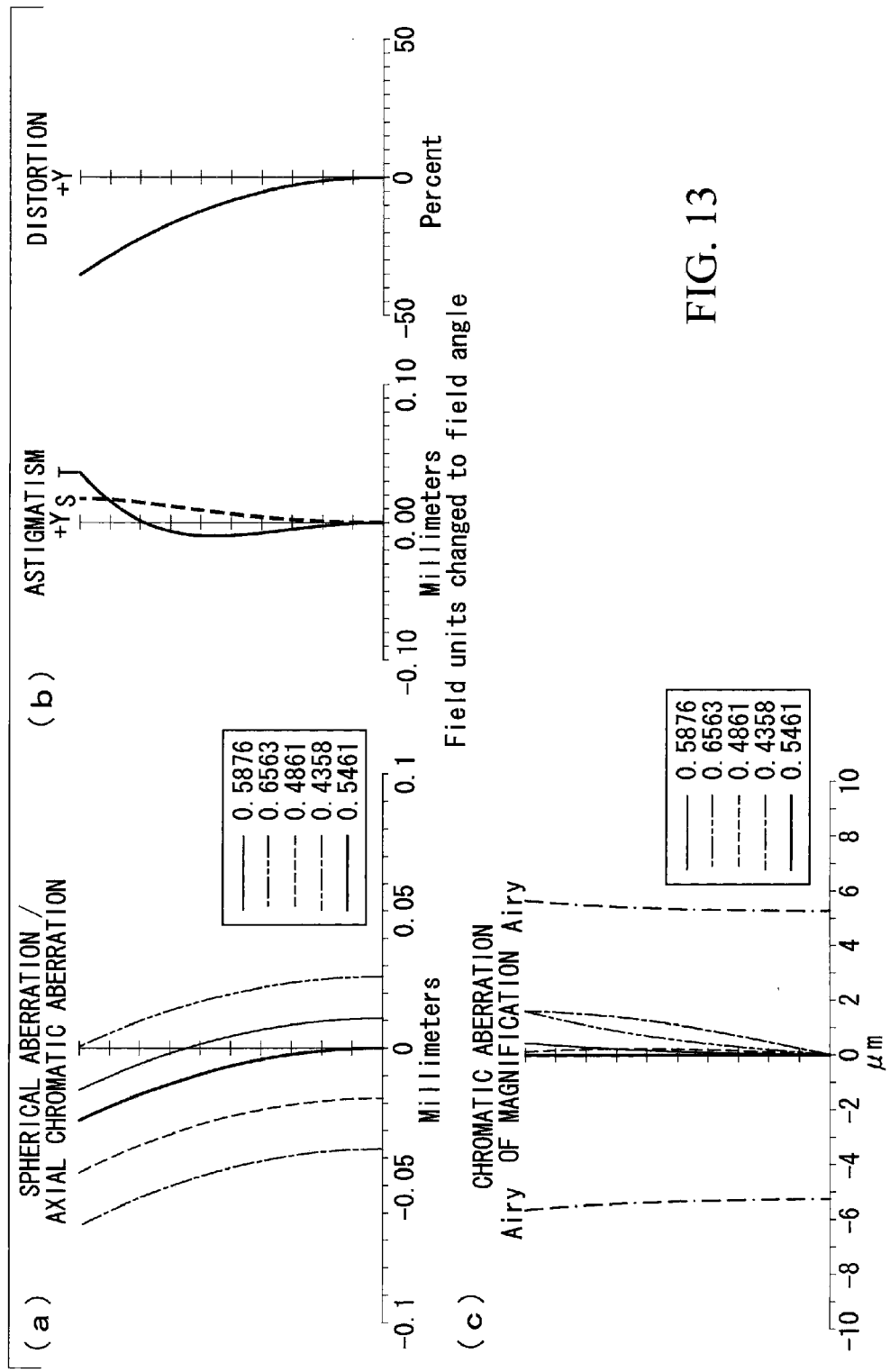
FIG. 13 is a diagram showing (a) spherical aberration/axial chromatic aberration, (b) astigmatism and distortion, and (c) magnification chromatic aberration of the endoscope objective optical system in FIG. 11 in a close-up observation state.
Figure 14:
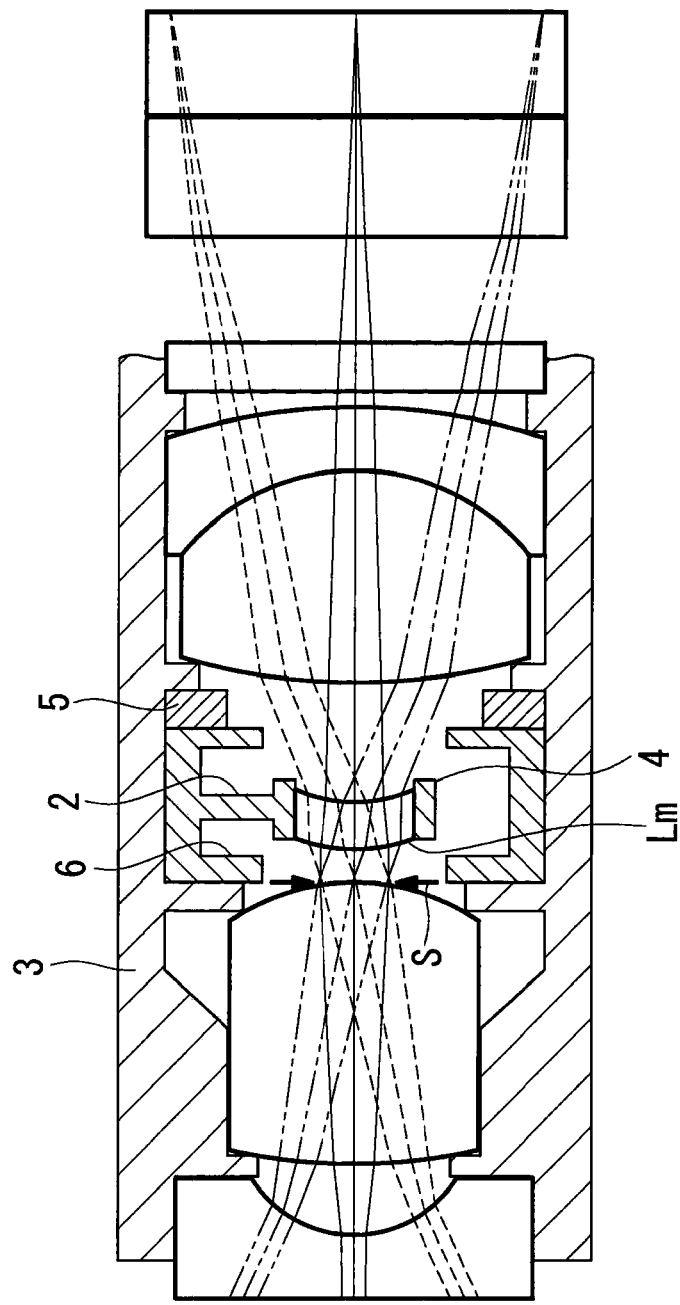
FIG. 14 is a diagram showing an example of a driving mechanism provided in the endoscope objective optical system in FIG. 11.

In the endoscope objective optical system of this example, FOVout/FOVin=1.23 holds, which satisfies Conditional Expression (2). Furthermore, the intersurface distance L between the front and back surfaces that flank the aperture stop is 1.015, which satisfies Conditional Expression (5). Various aberration diagrams of the endoscope objective optical system according to this example in the ordinary observation state and the close-up observation state are shown in FIGS. 12 and 13, respectively. An example of a configuration in which the objective optical system according to this example is provided with a driving mechanism for driving the meniscus lens is shown in FIG. 14.

| Lens Data | | | | | |
|---|---|---|---|---|---|
| Surface number | r | d | nd | vd | φ |
| OBJ | ∞ | d0 (variable) | | | 4.993 |
| 1 | ∞ | 0.330 | 1.883 | 40.8 | 0.950 |
| 2 | 0.644 | 0.376 | | | 0.545 |
| 3 | 3.038 | 1.474 | 1.67 | 47.2 | 0.661 |
| 4 | −1.172 | 0.025 | | | 0.661 |
| 5 (S) | ∞ | 0.025 | | | 0.182 |
| 6 | ∞ | 0.124 | | | 0.190 |
| 7 | 0.885 | 0.248 | 1.883 | 40.8 | 0.314 |
| 8 | 0.766 | 0.628 | | | 0.314 |
| 9 | 3.332 | 1.105 | 1.729 | 54.7 | 0.925 |
| 10 | −1.194 | 0.330 | 1.923 | 18.9 | 0.925 |
| 11 | −3.244 | 0.083 | | | 1.008 |
| 12 | ∞ | 0.256 | 1.494 | 75.0 | 1.008 |
| 13 | ∞ | 0.556 | | | 1.008 |
| 14 | ∞ | 0.620 | 1.516 | 64.1 | 1.115 |

-continued

| 15 | ∞ | 0.008 | 1.51 | 64.1 | 1.115 |
| 16 | ∞ | 0.537 | 1.504 | 60.0 | 1.115 |
| 17 | ∞ | 0.000 | | | 1.115 |
| IMG | ∞ | 0.000 | | | 0.997 |

Miscellaneous Data

| | Ordinary observation state | Close-up observation state |
|---|---|---|
| d0 | 10.740 | 3.305 |
| Full angle of view | 130° | 105.8° |
| Focal length of the entire system | 1.000 | 1.015 |

Example 6

An endoscope objective optical system according to Example 6 of the present invention is configured such that the meniscus lens in the lens configuration of Example 4 is replaced with a molded lens whose object-side surface (third surface) is an aspheric surface, and the other configuration is the same as that of Example 4. The lens data and miscellaneous data of the thus-configured endoscope objective optical system according to Example 6 are as follows:

The aspheric surface is defined by the following expression:

$$y = Cx^2[1+\{1-(1+K)\}^{1/2}C^2x^2] + A1x^4 + A2x^6 + A3x^8$$

Lens Data

| Surface number | r | d | nd | vd | φ |
|---|---|---|---|---|---|
| OBJ | ∞ | d0 (variable) | | | 5.721 |
| 1 | ∞ | 0.223 | 1.768 | 71.7 | 0.847 |
| 2 | 0.830 | 0.404 | | | 0.562 |
| 3* | −1.873 | 0.263 | 1.883 | 40.8 | 0.239 |
| 4 | −1.845 | 0.062 | | | 0.239 |
| 5 (S) | ∞ | 0.023 | | | 0.108 |
| 6 | ∞ | 0.306 | | | 0.108 |
| 7 | ∞ | 0.701 | 1.883 | 40.8 | 0.731 |
| 8 | −1.124 | 0.046 | | | 0.731 |
| 9 | 3.064 | 0.751 | 1.518 | 58.9 | 0.731 |
| 10 | −0.894 | 0.231 | 1.923 | 18.9 | 0.731 |
| 11 | −3.183 | 0.738 | | | 0.808 |
| 12 | ∞ | 0.239 | 1.523 | 58.6 | 0.962 |
| 13 | ∞ | 0.023 | | | 0.962 |
| 14 | ∞ | 0.239 | 1.51 | 75.0 | 0.962 |
| 15 | ∞ | 0.038 | | | 0.962 |
| 16 | ∞ | 0.385 | 1.516 | 64.1 | 0.962 |
| 17 | ∞ | 0.015 | 1.51 | 64.1 | 0.962 |
| 18 | ∞ | 0.500 | 1.506 | 50.2 | 1.046 |
| 19 | ∞ | 0.000 | | | 1.046 |
| IMG | ∞ | 0.000 | | | 0.933 |

Aspheric Surface Data

Third surface $C = -1.873$, $K = 24.858$
$A1 = -0.701$, $A2 = 18.219$, $A3 = -85.837$ Miscellaneous Data

| | Ordinary observation state | Close-up observation state |
|---|---|---|
| d0 | 6.933 | 2.927 |

Table 1 shows the values of Conditional Expressions (1) to (5) of the endoscope objective optical systems according to Examples 1 to 6 of the present invention described above.

TABLE 1

| Conditional Expression | Example 1 | Example 2 | Example 3 | Example 4 | Example 5 | Example 6 |
|---|---|---|---|---|---|---|
| (1) Fin/Fout | | 0.959 | | 0.975 | | |
| (2) FOVout/FOVin | | | 1.14 | | 1.23 | |
| (3) D/A | 2.851 | 2.090 | 1.879 | 2.213 | 1.725 | 2.210 |
| (4) P | 0.0392 | 0.0112 | −0.0386 | 0.0387 | −0.0031 | 0.039 |
| (5) L/Fout | 0.696 | 0.063 | 0.540 | 1.060 | 1.015 | 1.060 |

REFERENCE SIGNS LIST

1 endoscope objective optical system
FG front group
BG back group
S aperture stop
Lm, Lm' meniscus lens

The invention claimed is:

1. An endoscope objective optical system consisting of:
   a front group, an aperture stop, and a back group disposed in order from an object side; and
   a meniscus lens that can be inserted in and removed from an optical path between the aperture stop and the front group or the back group, with a convex surface thereof facing the aperture stop side.

2. The endoscope objective optical system according to claim 1, wherein
   the front group is a diverging lens system;
   the back group is a converging lens system;
   the meniscus lens can be inserted in and removed from the optical path between the aperture stop and the front group; and
   the following Conditional Expression (1) is satisfied:

$$0.9 \leq Fin/Fout \leq 1.1 \qquad (1)$$

where
   Fin: focal length of the entire system when the meniscus lens is inserted in the optical path,
   Fout: focal length of the entire system when the meniscus lens is retracted from the optical path.

3. The endoscope objective optical system according to claim 1, wherein
   the back group is a converging lens system;
   the meniscus lens can be inserted in and removed from between the aperture stop and the back group; and
   the following Conditional Expression (2) is satisfied:

$$1.1 < FOVout/FOVin < 1.5 \qquad (2)$$

where
FOVout: full angle of view when the meniscus lens is retracted from the optical path,
FOVin: full angle of view when the meniscus lens is inserted in the optical path.

4. The endoscope objective optical system according to claim 1, wherein the following Conditional Expression (3) is satisfied:

$$1.5 \leq D/A \leq 3 \quad (3)$$

where
A: inside diameter of the aperture stop,
D: outside diameter of the meniscus lens.

5. The endoscope objective optical system according to claim 1, wherein the meniscus lens satisfies the following Conditional Expression (4):

$$-0.1 \leq P \leq 0.1 \quad (4)$$

where
P: power of the meniscus lens.

6. The endoscope objective optical system according to claim 1, wherein the following Conditional Expression (5) is satisfied:

$$0.7 \leq L/Fout \leq 1.4 \quad (5)$$

where
L: intersurface distance between front and back lenses that flank the aperture stop,
Fout: focal length of the entire system when the meniscus lens is retracted from the optical path.

7. The endoscope objective optical system according to claim 1, wherein the meniscus lens is a molded lens.

8. The endoscope objective optical system according to claim 7, further comprising
an arm member that holds the meniscus lens and moves the meniscus lens between an inserted position at which the meniscus lens is inserted in the optical path and a retracted position at which the meniscus lens is retracted from the optical path, wherein
the arm member is integrally formed with the meniscus lens.

9. The endoscope objective optical system according to claim 1, wherein the effective F-number when the meniscus lens is retracted from the optical path is greater than or equal to 5.

10. The endoscope objective optical system according to claim 1, wherein the meniscus lens is constituted of a plurality of lenses.

* * * * *